United States Patent [19]

Ogata

[11] Patent Number: 4,742,163

[45] Date of Patent: May 3, 1988

[54] ALPHA-TOCOPHEROL (HALO)URIDINE PHOSPHORIC ACID DIESTER, SALTS THEREOF, AND METHODS FOR PRODUCING THE SAME

[75] Inventor: Kazumi Ogata, Toyonaka, Japan

[73] Assignee: Senju Pharmaceutical Co., Ltd., Osaka, Japan

[21] Appl. No.: 921,422

[22] Filed: Oct. 22, 1986

[30] Foreign Application Priority Data

Dec. 18, 1985 [JP] Japan ................... 60-284940

[51] Int. Cl.$^4$ .......................... C07H 19/10
[52] U.S. Cl. ...................... 536/29; 536/27; 536/28
[58] Field of Search ................ 536/27, 28, 29

[56] References Cited

U.S. PATENT DOCUMENTS 3,375,244  3/1968  Ouchi et al. ............. 536/28

FOREIGN PATENT DOCUMENTS

82/03079  9/1982  PCT Int'l Appl. ......... 536/29

Primary Examiner—J. R. Brown
Assistant Examiner—Jenny Tou
Attorney, Agent, or Firm—Wenderoth, Lind & Ponack

[57] ABSTRACT

A compound represented by the formula

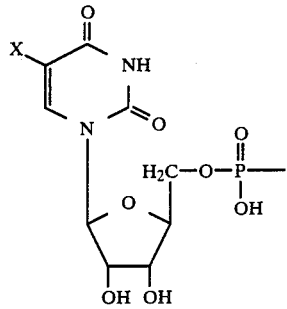

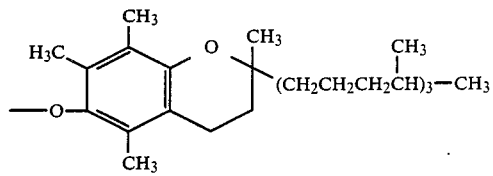

(wherein X represents a hydrogen atom or a halogen atom) provided in accordance with the invention are novel compounds of value as nonsteroidal antiinflammatory agents. Alpha-tocopherol 5-halouridine phosphoric acid diesters, in particular, are expected to be employable for antitumor agents as well.

4 Claims, 1 Drawing Sheet

ALPHA-TOCOPHEROL (HALO)URIDINE PHOSPHORIC ACID DIESTER, SALTS THEREOF, AND METHODS FOR PRODUCING THE SAME

BACKGROUND OF THE INVENTION

1. Field of the Invention

The present invention relates to alpha-tocopherol uridine phosphoric acid diester, halo-substituted derivatives thereof, and salts thereof, which are novel compounds of value as antiinflammatory agents, for instance, and methods for producing said compounds.

2. Description of the Prior Art

While a variety of antiinflammatory agents are known, it is generally acknowledged that steroidal antiinflammatory drugs are most effective. However, steroidal drugs tend to cause serious side effects and present several problems in clinical application. For this reason, various nonsteroidal antiinflammatory agents have been developed and put into use, but none of them are fully satisfactory.

The compounds provided in accordance with the present invention are phosphoric acid diesters of alpha-tocopherol and either uridine or uridine substituted by a halogen atom in its 5-position.

It is known that alpha-tocopherol is not only an effective antioxidant for unsaturated fatty acids but has many pharmacological and physiological activities such as peripheral vasodilator activity, antiarteriosclerotic activity and so on. Recently, it has been suggested that this compound is effective in the treatment of cataract as well.

On the other hand, uridine is a constituent of ribonucleic acid and 5-halouridines have been known to display antitumor activity in vivo. However, there has not been known a compound consisting of alpha-tocopherol and either uridine or a 5-halouridine, all of which have such varied and benificial properties, as linked through the intermediary of a phosphoric acid moiety.

The present inventor synthesized a variety of compounds, screened them for new and highly effective nonsteroidal antiinflammatory agents, and ultimately discovered that the phosphoric acid diester of alpha-tocopherol and either uridine or 5-halouridine is a very desirable antiinflammatory agent. The present invention has been accomplished on the basis of the above finding.

SUMMARY OF THE INVENTION

It is an object of the present invention to provide novel compounds having antiinflammatory activity.

It is another object of the present invention to provide compounds which are promising as antitumor agents, for instance.

DETAILED DESCRIPTION OF THE INVENTION

Figure 1:
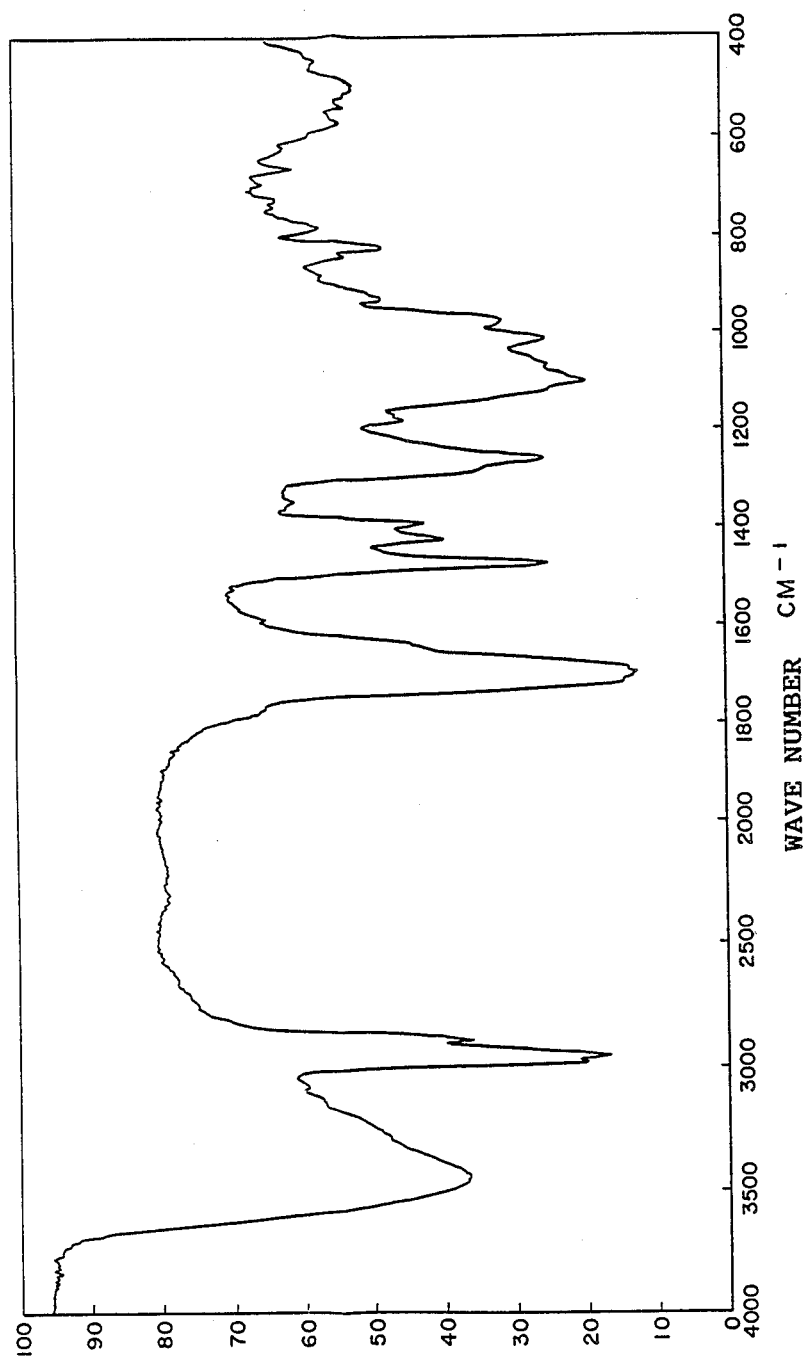
FIG. 1 is the infrared absorption spectrum (KBr disk) of DL-alpha-tocopherol uridine phosphoric acid diester.

The compound according to the present invention has the structure represented by the following formula.

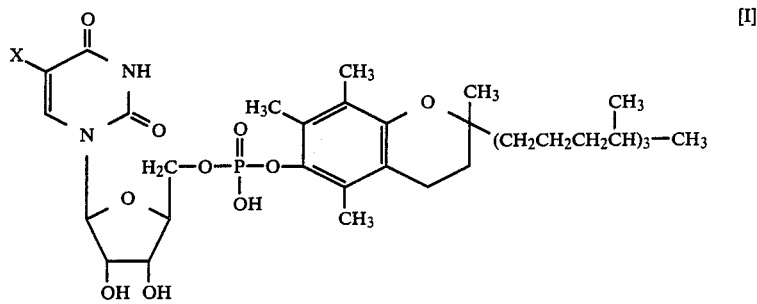

(wherein X represents a hydrogen atom or halogen atom.)

The present invention is directed to a phosphoric acid diester of formula [I] or a salt thereof and a method of producing a phosphoric acid diester of formula [I] which comprises reacting alpha-tocopherol with a halophosphorylating agent, reacting the resulting compound further with either uridine with its 2'- and 3'-hydroxyl groups protected or a 5-halosubstituted derivative thereof, and finally deprotecting the resulting compound.

In the production method according to the present invention, alpha-tocopherol is first reacted with a halophosphorylating agent. While this halophosphorylating agent may be any compound that is able to halophosphorylate the hydroxyl group of alpha-tocopherol, it is particularly advantageous to use a phosphorus oxyhalide such as phosphorus oxychloride, phosphorus oxybromide or the like.

This reaction can be advantageously conducted in an inert solvent such as benzene or toluene in the presence of an acid acceptor. As the acid acceptor, an organic amine such as pyridine, triethylamine or the like can be generally employed. When phosphorus oxychloride, for instance, is used as the halophosphorylating agent, the reaction may be written as follows.

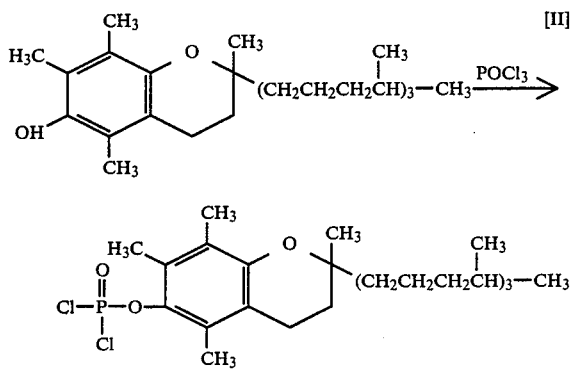

Alpha-tocopherol, which is submitted to the reaction, may be either of the DL-form and L-form, there being no difference in reaction yield therebetween.

The resulting compound [II] is further reacted with either uridine with its 2'- and 3'-hydroxyl groups protected with, e.g. an isopropylidene group, or a 5-halo-substituted derivative thereof [III].

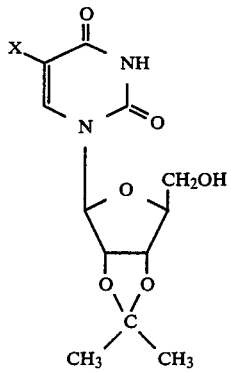

(wherein X represents the same group as mentioned above)

The protective groups for the 2'- and 3'-hydroxyl groups of said uridine or uridine-5-halide may be chosen from among the many protective groups known in the art of nucleic acid chemistry, and most generally, isopropylidene or the like groups and acyl groups such as acetyl may be employed. This reaction may be conducted advantageously in appropriate inert organic solvent. As the solvent for this reaction, tetrahydrofuran and the like are generally desirable but another solvent that does not interfere with this reaction may also be employed. The deprotection reaction may be conducted under mild conditions. For example, the protective groups may be easily removed by acidifying the reaction mixture with hydrochloric acid. It is supposed that, in the first stage, one chlorine (halogen) atom in the compound [II] is substituted for by compound [III], and then the remaining chlorine (halogen) is replaced by hydroxyl group through hydrolysis during the deprotection reaction.

The above procedure gives the compound [I] of the present invention. The compound of the present invention affords better crystallinity in the salt form than in the free acid form. As regards the salt, sodium and potassium salts of compound [I] are readily soluble in water but the calcium salt is not. For conversion of free acid to such as alkali metal salt, for instance, neutralization with an alkali metal hydroxide is a generally preferred procedure. The halogen atom of the alpha-tocopherol 5-halouridine phosphoric acid diester according to present invention may for example be chlorine, bromine, fluorine or iodine.

Either in the free acid form or in the form of a suitable salt, the compound according to the present invention can be formulated into various dosage forms, such as injections, ophthalmic solutions (eye drops), tablets, capsules, ointments, creams, etc., by the established pharmaceutical procedures.

The concentration of the compound [I] in the above drugs varies depending on the dosage forms and disease conditions, but is in the range of from about 0.005 to about 30%, preferably about 0.01% to about 10%. For example, in case of injections, the concentration is about 0.01 to about 0.1%, and the content of the compound [I] in ointments is about 1 to about 10%. For oral administration, the daily dose is about 100 mg to about 1000 mg for adult humans.

The preparation of this invention may be incorporated with a usually employable amount of additives conventionally usable for pharmaceutical preparations, for example, preservatives (benzalkonium chloride, cetylpiperidium chloride, chlorobutanol, methylparaben, propylparaben, etc.), excipients (starch, lactose, etc.), nonionic surfactants (polyoxyethylene sorbitan monooleate, polyoxyethylene stearyl triglyceride, polyethylene glycol, etc.) and so forth. Also, other pharmaceutically active ingredients may be further contained without impairment of this invention.

The compound according to the present invention is stable at room temperature. Therefore, it can be provided as stable pharmaceutical preparations and it can be expected that only in vivo the phosphoric acid diester linkages between phosphoric acid and the other components are cleaved off by phosphatase, phosphodiesterase or the like to liberate alpha-tocopherol and uridine or its 5-halo-substituted derivative and thereby allow the effects of the constituent compounds to be developed in the recipient's body.

The above-mentioned alpha-tocopherol uridine phosphoric acid diester and 5-halo-substituted derivatives thereof, which are provided in accordance with the present invention, have antiinflammatory and other activities.

The following examples are intended to illustrate the invention in further detail.

EXAMPLE 1

DL-alpha-tocopherol uridine phosphoric acid diester

In 50 ml of benzene is dissolved 6.12 g of phosphoric oxychloride and, then, a mixed solution of 8.6 g (0.02 mol) DL-alpha-tocopherol and 9.5 g of pyridine in 50 ml of benzene is added dropwise under stirring. The mixture is further stirred for 3 hours, after which the precipitated pyridine hydrochloride is filtered off. The filtrate is concentrated under reduced pressure at 50° C. and the oily residue is dissolved in 30 ml of benzene. Separately, 6.82 g (0.024 mol) of isopropylideneuridine and 3.2 g of pyridine are dissolved in 120 ml of tetrahydrofuran. Then, under ice-cooling and stirring, the above benzene solution is added dropwise thereto. Thereafter, the mixture is stirred at the same temperature for about 1 hour and, then, at room temperature for about 1 hour. The precipitated pyridine hydrochloride is filtered off and the filtrate is concentrated under reduced pressure. The oily residue is dissolved in 30 ml of ethanol, followed by addition of 150 ml of 1N hydrochloric acid. The mixture is refluxed for about 15 minutes and, then, cooled. The reaction mixture is extracted with ethyl acetate and extract is dried over anhydrous sulfate. The ethyl acetate is then distilled off and residue is dissolved in about 100 ml of anhydrous ethanol. Under stirring, a saturated aqueous solution of sodium hydroxide is added dropwise thereto until the solution becomes neutral. The resulting white crystals are collected by filtration, washed with ethanol and recrystallized from water-ethanol to give 8.5 g of DL-alpha-tocopherol uridine phosphoric acid diester sodium salt which melts at 246°–248° C. (decompn.).

Elementary Analysis for $C_{38}H_{60}O_{10}N_2Na.\frac{1}{2}H_2O$: Calcd.: C, 59.44%; H, 8.01%; N, 3.65%. Found: C, 59.24%; H, 8.12%; N, 3.48%.

The above sodium salt is dissolved in water and the solution is acidified with hydrochloric acid to give DL-alpha-tocopherol-uridine phosphoric acid diester as white crystals. The infrared absorption spectrum (KBr disk) of this product is shown in FIG. 1.

EXAMPLE 2

DL-alpha-tocopherol 5-bromouridine phosphoric acid diester

The phosphrylation reaction described in Example 1 is repeated except that 4.3 g (0.01 mol) of DL-alpha-tocopherol, 4 g of pyridine, 3.06 g of phosphorus oxychloride, and 50 ml of benzene are used. Separately, 5-bromouridine is treated with p-toluene-sulfonic acid in aceton to give isopropylidene-5-bromouridine and 4.35 g (0.012 mol) of this isopropylidene-5-bromouridine and 2 g of pyridine are dissolved in 60 ml of tetrahydrofuran. Then, the reaction and workup procedures of Example 1 are followed to give the potassium salt and, then, the free acid. The free acid is recrystallized from ethanol to give 2.5 g of colorless crystals melting at 177°–178° C.

Elementary Analysis for $C_{38}H_{60}O_{10}N_2PBr$: Calcd.: C, 55.95%; H, 7.41%; N, 3.43%. Found: C, 55.76%; H, 7.53%; N, 3.24%.

PREPARATION EXAMPLE 1

Ophthalmic solution

| | |
|---|---|
| DL-alpha-tocopherol uridine phosphoric acid diester sodium salt | 0.3 g |
| Boric acid | 1.5 g |
| Borax | 0.3 g |
| Methyl p-hydroxybenzoate | 0.026 g |
| Propyl p-hydroxybenzoate | 0.014 g |
| Sterile purified water | (To make a total of 100 ml) |

The above ingredients are mixed to prepare an ophthalmic solution.

PREPARATION EXAMPLE 2

Injection

| | |
|---|---|
| DL-alpha-tocopherol uridine phosphoric acid diester sodium salt | 0.02 g |
| Glucose | 5 g |
| Distilled water for injection | (To make a total of 100 ml) |

Using the above ingredients, the established preparation procedure for injections is followed to provide an injectable solution.

PREPARATION EXAMPLE 3

Tablet

| | |
|---|---|
| DL-alpha-tocopherol 5-bromouridine phosphoric acid diester calcium salt | 100 mg |
| Lactose | 80 mg |
| Starch | 17 mg |
| Magnesium stearate | 3 mg |

The above ingredients, as a raw material for one tablet, are molded into a tablet by the conventional method. The tablet may be coated with sugar, if necessary.

What is claimed is:

1. A phosphoric acid diester of the formula

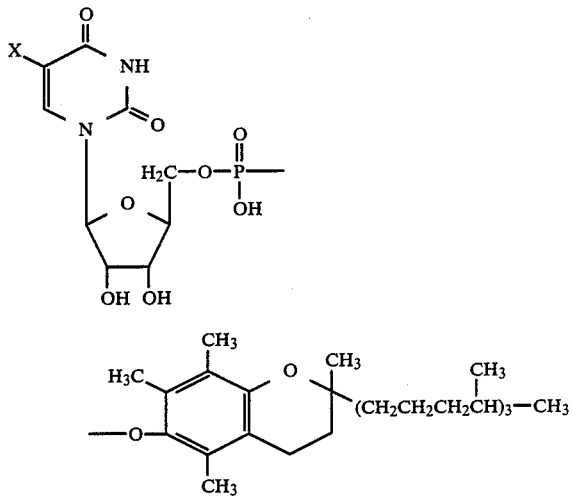

wherein X represents a hydrogen atom or a halogen atom, or an alkali metal or calcium salt thereof.

2. The phosphoric acid diester claimed in claim 1, wherein X represents a hydrogen atom.

3. The phosphoric acid diester claimed in claim 1, wherein X represents a halogen atom.

4. The phosphoric acid diester claimed in claim 3, wherein the halogen atom is bromine.

* * * * *